US012694976B2

(12) United States Patent
Agnello et al.

(10) Patent No.: US 12,694,976 B2
(45) Date of Patent: Jul. 28, 2026

(54) MEDICAL DEVICE LOCATION AND TRACKING SYSTEM

(71) Applicant: Abiomed, Inc., Danvers, MA (US)

(72) Inventors: Alessandro Simone Agnello, Peabody, MA (US); Gregory John Eichmann, North Reading, MA (US); Paul Roland Lemay, Nashua, NH (US)

(73) Assignee: ABIOMED, INC., Danvers, MA (US)

( * ) Notice: Subject to any disclaimer, the term of this patent is extended or adjusted under 35 U.S.C. 154(b) by 170 days.

(21) Appl. No.: 16/370,951

(22) Filed: Mar. 30, 2019

(65) Prior Publication Data

US 2020/0312450 A1 Oct. 1, 2020

(51) Int. Cl.
*G16H 40/67* (2018.01)
*G05B 13/02* (2006.01)

(52) U.S. Cl.
CPC ......... *G16H 40/67* (2018.01); *G05B 13/0265* (2013.01)

(58) Field of Classification Search
CPC ........ G16H 40/67; G16H 40/00; G16H 40/20; G16H 40/40; G16H 40/60; G05B 13/0265; G06N 20/00
USPC ........................................................ 705/2–3
See application file for complete search history.

(56) References Cited

U.S. PATENT DOCUMENTS

2005/0246092 A1* 11/2005 Moscatiello .......... G01S 5/0072
701/408
2006/0279427 A1* 12/2006 Becker ................... G16H 40/20
340/573.4

2007/0080801 A1* 4/2007 Weismiller ................ G01S 5/02
340/539.13
2007/0106518 A1* 5/2007 Wildman ........... G08B 13/2462
455/95
2008/0169927 A1* 7/2008 Graves ................... G16H 40/63
340/572.1
2010/0305966 A1* 12/2010 Coulter ................. G06Q 10/06
705/2
2011/0237185 A1* 9/2011 Murray ................. H04W 4/023
455/41.1
2014/0219548 A1* 8/2014 Wels ...................... G06F 18/28
382/154

(Continued)

FOREIGN PATENT DOCUMENTS

JP 2016076160 A 5/2016

OTHER PUBLICATIONS

Osvaldo Simeone, A Very Brief Introduction to Machine Learning With Applications to Communication Systems, IEEE Transactions on Cognitive Communications and Networking, vol. 4, No. 4, Dec. 2018, 17 pages (Year: 2018).*

(Continued)

*Primary Examiner* — Jason S Tiedeman
(74) *Attorney, Agent, or Firm* — Botos Churchill IP Law LLP

(57) ABSTRACT

Methods and systems for automatically ascertaining physical location information about a plurality of medical device controllers and tracking changes in the physical locations of ones of the respective medical device controllers. One or more machine learning modules infer the physical locations from computer network messages received from the medical device controllers, including information about computer network components that are proximate ones of the medical device controllers.

20 Claims, 9 Drawing Sheets

(56)      References Cited

U.S. PATENT DOCUMENTS

| | | | |
|---|---|---|---|
| 2014/0358574 A1 | 12/2014 | Tara et al. | |
| 2014/0371816 A1* | 12/2014 | Matos | A61N 1/39622 |
| | | | 607/59 |
| 2015/0081335 A1* | 3/2015 | Dixon | G16H 40/20 |
| | | | 705/2 |
| 2015/0151051 A1 | 6/2015 | Tsoukalis | |
| 2016/0371639 A1 | 12/2016 | Smith et al. | |
| 2017/0011181 A1* | 1/2017 | McNeely | G16H 40/20 |
| 2017/0242968 A1* | 8/2017 | Kiukkonen | H04L 67/10 |
| 2019/0007793 A1* | 1/2019 | Liang | G06N 3/084 |
| 2019/0209258 A1* | 7/2019 | Stockdale | G16H 40/20 |
| 2019/0228863 A1* | 7/2019 | Dharwad | G16H 40/40 |
| 2019/0244707 A1* | 8/2019 | Becker | H04L 67/52 |
| 2020/0335190 A1* | 10/2020 | Chung | A61B 5/0022 |

OTHER PUBLICATIONS

Hurwitz et al., Machine Learning for Dummies, IBM Limited Edition, John Wiley & Sons, Inc., 75 pages (Year: 2018).*

Hu et al., Harnessing Deep Neural Networks with Logic Rules, Proceedings of the 54th Annual Meeting of the Association for Computational Linguistics, pp. 2410-2420 (Year: 2016).*

Training ML Models—Amazon Machine Learning, no author, one page (Year: 2017).*

Hayhurst, Christopher, Seek and You Shall Find? Tracking Medical Devices in Healthcare Facilities, Advancing Safety in Health Technology, Biomedical Instrumentation & Technology, 10 pages (Year: 2018).*

Prem, A Simple Introduction to Online Machine Learning, website, 12 pages (Year: 2023).*

Unknown author, Deep Learning Training vs. Inference, What's the Difference, webpage, 11 pages (Year: 2023).*

Sydoranko, Iryna, How to Use Unlabeled Data in Machine Learning, website, 21 pages (Year: 2020).*

Unknown author, Training versus Inference, webpage, 4 pages (Year: 2019).*

Joby, Amal, Unsupervised Learning: How Machines Learn on Their Own, website, 8 pages (Year: 2021).*

International Searching Authority—International Search Report—International Application No. PCT/US2020/025731, dated Jul. 3, 2020, together with the Written Opinion of the International Searching Authority, 18 pages.

Office Action from corresponding Indian Patent Application No. 202117047530 dated Sep. 11, 2023.

Office Action from corresponding Israeli Patent Application No. 286772 dated Dec. 5, 2024 (3 pp.).

Written Opinion from corresponding Singapore Patent Application No. 11202110351X dated Nov. 21, 2024 (5 pp.).

Office Action from corresponding Australian Patent Application No. 2020256141, dated Jan. 21, 2025 (4 pp.).

Office Action from corresponding Canadian Patent Application No. 3, 131,353 dated Apr. 15, 2025 (7 pp.).

Office Action from corresponding Korean Patent Application No. 10-2021-7035670 dated Nov. 14, 2025 (16 pp.).

Office Action from corresponding Singapore Patent Application No. 11202110351X, dated Aug. 19, 2025 (7 pp.).

Office Action issued in Australian Patent Application No. 2020256141, dated Dec. 23, 2025 (3 pp.).

* cited by examiner

MEDICAL DEVICE LOCATION AND TRACKING SYSTEM

BACKGROUND

Technical Field

The present invention relates to medical device location and tracking systems and, more particularly, to machine learning-based systems that automatically associate network identifiers used by medical devices to report status information with physical locations and thereby automatically detect when the medical devices are moved to other physical locations.

Related Art

Many medical devices, such as some implanted heart pumps, for example the Impella® 2.5 hear pump available from Abiomed, Inc., Danvers, MA, are connected to external controllers that collect and display operational data about the medical devices, such as heart signal level, battery temperature, blood flow rate and plumbing integrity. Exemplary controllers are available from Abiomed, Inc. under the trade name Automated Impella Controller®. The controllers raise alarms when operational data values fall beyond predetermined values or ranges, for example if a leak or loss of suction is detected. These controllers include video display screens as human interfaces, on which the operational data and/or alarms are displayed.

To facilitate remote monitoring by medical personnel to ensure efficacy and patient safety, some such controllers may be coupled via computer networks, often including wireless segments, to central servers, which may be accessed by monitoring stations. The monitoring stations may display real-time and/or historical operational data and/or alarms on display screens for viewing by the medical personnel.

Many such controllers are expensive and/or in short supply in hospitals and other healthcare facilities. Consequently, as these controllers become available, such as after a heart pump is removed from a patient, these organizations often move these controllers to where the controllers are needed, including moving the controllers among floors of a building, between buildings on a campus and between campuses. In addition, sometimes these controllers are moved along with patients, while attached medical devices are still connected to the patients, such as if a patient is moved from an operating room to an intensive care unit.

However, this movement causes problems for the medical personnel who remotely monitor the controllers and their attached medical devices. Although the user interfaces of some controllers facilitate entering location information, such information is not always entered when the controllers are moved, and sometimes the information is entered incorrectly. Thus, if a controller is moved, for example from one room or floor or building to another, the medical personnel remotely monitoring the controller may have no way to learn of the new location.

Lack of, or incorrect, information about the physical location of a controller can jeopardize patient safety. For example, if the medical personnel remotely monitoring an implanted heart pump become aware of an unsafe condition, such as because the corresponding controller raises an alarm, but the medical personnel do not know the (correct) location, such as room number, where the patient with the implanted heart pump is currently located, the medical personnel cannot quickly dispatch a nurse, doctor or technician, as the case may be, to the patient.

SUMMARY OF EMBODIMENTS

An embodiment of the present invention provides a medical device controller location and tracking system. The system includes a first electronic data store, a second electronic data store, a user interface and a first machine learning module.

The first electronic data store is configured to store a plurality of first entries. Each first entry contains information that associates a respective medical device controller with a respective physical location. The second electronic data store is configured to store a plurality of second entries. Each second entry contains information that associates a respective computer network device with a respective physical location.

The user interface is configured to receive information identifying an identified medical device controller. The information identifying the identified medical device controller may be entered by a human, or the information identifying the identified medical device controller may be automatically ascertained, without human input into the user interface. The user interface is also configured to receive information, from a human user, identifying an entered physical location of the identified medical device controller. The user interface is configured to store a new first entry in the first electronic data store. The new first entry associates the identified medical device controller with the entered physical location.

The receiver is configured to receive messages from a plurality of medical device controllers. The receiver is configured to receive the messages via a computer network. Each message is sent by a respective sender medical device controller of the plurality of medical device controllers. Each message includes an identifier of the sender medical device controller. Each message also includes an identifier of a computer network device.

The first machine learning module is configured, in response to receipt of ones of the messages, to automatically determine whether an entry in the first electronic data store associates the sender medical device controller with a respective physical location. In other words, the first machine learning module is configured to automatically determine whether the first electronic data store contains such an association, not whether the sender medical device controller is associated with a particular physical location. If an entry in the first electronic data store is found that associates the sender medical device controller with a respective physical location, the first machine learning module is configured to store a new second entry in the second electronic data store. The new second entry associates the computer network device with the physical location associated with the sender medical device controller.

In any embodiment, the identifier of the computer network device may identify a computer network device with which the sender medical device controller has communicated. The identifier of the computer network device may identify a computer network device with which the sender medical device controller has directly communicated wirelessly. The identifier of the computer network device may identify a wireless access point with which the sender medical device controller has directly communicated wirelessly. The identifier of the computer network device may include a base station identifier of a cellular base station with which the sender medical device controller has directly communicated wirelessly. The identifier of the computer network device may identify a computer network device through which the message traveled en route to the receiver. The identifier of the computer network device may include an IP address.

In any embodiment, the medical device controller location and tracking system may include a second machine learning module. The second machine learning module may be configured, in response to receipt of ones of the messages, to automatically determine whether an entry in the first electronic data store associates the sender medical device controller with a respective physical location. If no entry in the first electronic data store is found that associates the sender medical device controller with a respective physical location, the second machine learning module may be configured to determine whether an entry in the second electronic data store associates the computer network device with a respective physical location.

If no entry in the first electronic data store is found that associates the sender medical device controller with a respective physical location and an entry in the second electronic data store is found that associates the computer network device with a respective physical location, the second machine learning module may be configured to store a new first entry in the first electronic data store. The new first entry may associate the sender medical device controller with the physical location associated with the computer network device.

In any embodiment, the medical device controller location and tracking system may include a third machine learning module. The third machine learning module may be configured, in response to receipt of ones of the messages, to automatically determine whether an entry in the first electronic data store associates the sender medical device controller with a respective physical location. If an entry in the first electronic data store is found that associates the sender medical device controller with a respective physical location, the third machine learning module may be configured to determine whether an entry in the second electronic data store associates the computer network device with a respective physical location.

If an entry in the first electronic data store is found that associates the sender medical device controller with a respective physical location and an entry in the second electronic data store is found that associates the computer network device with a respective physical location, the third machine learning module may be configured to compare the physical location associated with the sender medical device controller in the first electronic data store to the physical location associated with the computer network device in the second electronic data store.

If an entry in the first electronic data store is found that associates the sender medical device controller with a respective physical location and an entry in the second electronic data store is found that associates the computer network device with a respective physical location and the physical location associated with the sender medical device controller in the first electronic data store is found to differ from the physical location associated with the computer network device in the second electronic data store, the third machine learning module may be configured to revise the entry in the first electronic data store to associate the sender medical device controller with the physical location associated with the computer network device in the second electronic data store.

In any embodiment, the third machine learning module may be configured to temporarily revise the entry in the first electronic data store to associate the sender medical device controller with the physical location associated with the computer network device in the second electronic data store. The third machine learning module may be further configured to automatically subsequently revise the entry in the first electronic data store to associate the sender medical device controller with a default value.

Another embodiment of the present invention provides a medical device controller location and tracking system. The system includes a first electronic data store, a second electronic data store, a receiver and a second machine learning module.

The first electronic data store is configured to store a plurality of first entries. Each first entry contains information that associates a respective medical device controller with a respective physical location. The second electronic data store configured to store a plurality of second entries Each second entry contains information that associates a respective computer network device with a respective physical location.

The receiver is configured to receive messages from a plurality of medical device controllers. The receiver is configured to receive the messages via a computer network. Each message is sent by a respective sender medical device controller of the plurality of medical device controllers. Each message includes an identifier of the sender medical device controller. Each message also includes an identifier of a computer network device.

The second machine learning module is configured, in response to receipt of ones of the messages, to automatically determine whether an entry in the first electronic data store associates the sender medical device controller with a respective physical location. If no entry in the first electronic data store is found that associates the sender medical device controller with a respective physical location, the second machine learning module is configured to automatically determine whether an entry in the second electronic data store associates the computer network device with a respective physical location.

If no entry in the first electronic data store is found that associates the sender medical device controller with a respective physical location and an entry in the second electronic data store is found that associates the computer network device with a respective physical location, the second machine learning module is configured to automatically store a new first entry in the first electronic data store. The new first entry associates the sender medical device controller with the physical location associated with the computer network device.

Yet another embodiment of the present invention provides a medical device controller location and tracking system. The system includes a first electronic data store, a second electronic data store, a receiver and a third machine learning module.

The first electronic data store is configured to store a plurality of first entries. Each first entry contains information that associates a respective medical device controller with a respective physical location. The second electronic data store is configured to store a plurality of second entries. Each second entry contains information that associates a respective computer network device with a respective physical location.

The receiver is configured to receive messages from a plurality of medical device controllers. The receiver is configured to receive the messages via a computer network.

Each message is sent by a respective sender medical device controller of the plurality of medical device controllers. Each message includes an identifier of the sender medical device controller. Each message also includes an identifier of a computer network device.

The third machine learning module is configured, in response to receipt of ones of the messages, to automatically determine whether an entry in the first electronic data store associates the sender medical device controller with a respective physical location. If an entry in the first electronic data store is found that associates the sender medical device controller with a respective physical location, the third machine learning module is configured to determine whether an entry in the second electronic data store associates the computer network device with a respective physical location.

If an entry in the first electronic data store is found that associates the sender medical device controller with a respective physical location and an entry in the second electronic data store is found that associates the computer network device with a respective physical location, the third machine learning module is configured to compare the physical location associated with the sender medical device controller in the first electronic data store to the physical location associated with the computer network device in the second electronic data store.

If an entry in the first electronic data store is found that associates the sender medical device controller with a respective physical location and an entry in the second electronic data store is found that associates the computer network device with a respective physical location and the physical location associated with the sender medical device controller in the first electronic data store is found to differ from the physical location associated with the computer network device in the second electronic data store, the third machine learning module is configured to revise the entry in the first electronic data store to associate the sender medical device controller with the physical location associated with the computer network device in the second electronic data store.

An embodiment of the present invention provides a method for locating and tracking medical device controllers. The method includes providing first and second electronic data stores. The first electronic data store is configured to store a plurality of first entries. Each first entry contains information that associates a respective medical device controller with a respective physical location. The second electronic data store is configured to store a plurality of second entries. Each second entry contains information that associates a respective computer network device with a respective physical location.

Information identifying an identified medical device controller is received.

Information identifying an entered physical location of the identified medical device is received from a human user, via a user interface.

A new first entry is stored in the first electronic data store The new first entry associates the identified medical device controller with the entered physical location.

A message is received from a sender medical device controller. The message is received via a computer network. The message includes an identifier of the sender medical device controller. The message also includes an identifier of a computer network device.

In response to receipt of the message, a determination is automatically made to ascertain whether an entry in the first electronic data store associates the sender medical device with a respective physical location. If an entry in the first electronic data store is found that associates the sender medical device controller with a respective physical location, a new second entry is stored in the second electronic data store. The new second entry associates the computer network device with the physical location associated with the sender medical device controller.

In any embodiment, receiving the message that includes the identifier of the computer network device may include receiving a message that identifies a computer network device with which the sender medical device controller has communicated. In any embodiment, receiving the message that includes the identifier of the computer network device may include receiving a message that identifies a computer network device with which the sender medical device controller has directly communicated wirelessly. In any embodiment, receiving the message that includes the identifier of the computer network device may include receiving a message that identifies a wireless access point with which the sender medical device controller has directly communicated wirelessly. In any embodiment, receiving the message that includes the identifier of the computer network device may include receiving a message that identifies a base station identifier of a cellular base station with which the sender medical device controller has directly communicated wirelessly. In any embodiment, receiving the message that includes the identifier of the computer network device may include receiving a message that identifies a computer network device through which the message traveled en route to the receiver. In any embodiment, receiving the message that includes the identifier of the computer network device may include receiving a message that identifies an IP address.

In any embodiment, in response to receipt of the message, a determination may be automatically made to ascertain whether an entry in the first electronic data store associates the sender medical device controller with a respective physical location. If no entry in the first electronic data store is found that associates the sender medical device controller with a respective physical location, a determination may be automatically made to ascertain whether an entry in the second electronic data store associates the computer network device with a respective physical location.

If no entry in the first electronic data store is found that associates the sender medical device controller with a respective physical location and an entry in the second electronic data store is found that associates the computer network device with a respective physical location, a new first entry may be stored in the first electronic data store. The new first entry may associate the sender medical device controller with the physical location associated with the computer network device.

In any embodiment, in response to receipt of the message, a determination may be automatically made to ascertain whether an entry in the first electronic data store associates the sender medical device controller with a respective physical location. If an entry in the first electronic data store is found that associates the sender medical device controller with a respective physical location, a determination may be automatically made to ascertain whether an entry in the second electronic data store associates the computer network device with a respective physical location.

If an entry in the first electronic data store is found that associates the sender medical device controller with a respective physical location and an entry in the second electronic data store is found that associates the computer network device with a respective physical location, the physical location associated with the sender medical device controller in the first electronic data store maybe compared to the physical location associated with the computer network device in the second electronic data store.

If an entry in the first electronic data store is found that associates the sender medical device controller with a respective physical location and an entry in the second electronic data store is found that associates the computer network device with a respective physical location and the physical location associated with the sender medical device controller in the first electronic data store is found to differ from the physical location associated with the computer network device in the second electronic data store, the entry in the first electronic data store may be revised to associate the sender medical device controller with the physical location associated with the computer network device in the second electronic data store.

In any embodiment, revising the entry in the first electronic data store to associate the sender medical device controller with the physical location associated with the computer network device in the second electronic data store may include temporarily revising the entry in the first electronic data store to associate the sender medical device controller with the physical location associated with the computer network device in the second electronic data store, and then automatically revising the entry in the first electronic data store to associate the sender medical device controller with a default value.

Yet another embodiment of the present invention provides a non-transitory computer-readable medium. The non-transitory computer-readable medium is encoded with instructions. When executed by a processor, the instructions establish processes for performing a computer-implemented method for locating and tracking medical device controllers. The processes include a process configured to provide a first electronic data store and a process configured to provide a second electronic data store.

The first electronic data store is configured to store a plurality of first entries. Each first entry contains information that associates a respective medical device controller with a respective physical location. The second electronic data store is configured to store a plurality of second entries. Each second entry contains information that associates a respective computer network device with a respective physical location.

A process is configured to receive information identifying an identified medical device controller.

A process configured to receive information identifying an entered physical location of the identified medical device. The process is configured to receive the information from a human user, via a user interface.

A process is configured to store a new first entry in the first electronic data store. The new first entry associates the identified medical device controller with the entered physical location.

A process is configured to receive a message from a sender medical device controller. The process is configured to receive the message via a computer network. The message includes an identifier of the sender medical device controller. The message also includes an identifier of a computer network device.

A process is configured, in response to receipt of the message, to automatically determine whether an entry in the first electronic data store associates the sender medical device with a respective physical location.

A process configured, if an entry in the first electronic data store is found that associates the sender medical device controller with a respective physical location, to store a new second entry in the second electronic data store, wherein the new second entry associates the computer network device with the physical location associated with the sender medical device controller.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Embodiments of the present invention provide methods and systems for automatically ascertaining physical location information about a plurality of medical device controllers and tracking changes in the physical locations of ones of the respective medical device controllers. These embodiments utilize one or more machine learning modules to infer the physical locations from computer network messages received from the medical device controllers, including information about computer network components that are proximate ones of the medical device controllers.

Context

Figure 1:
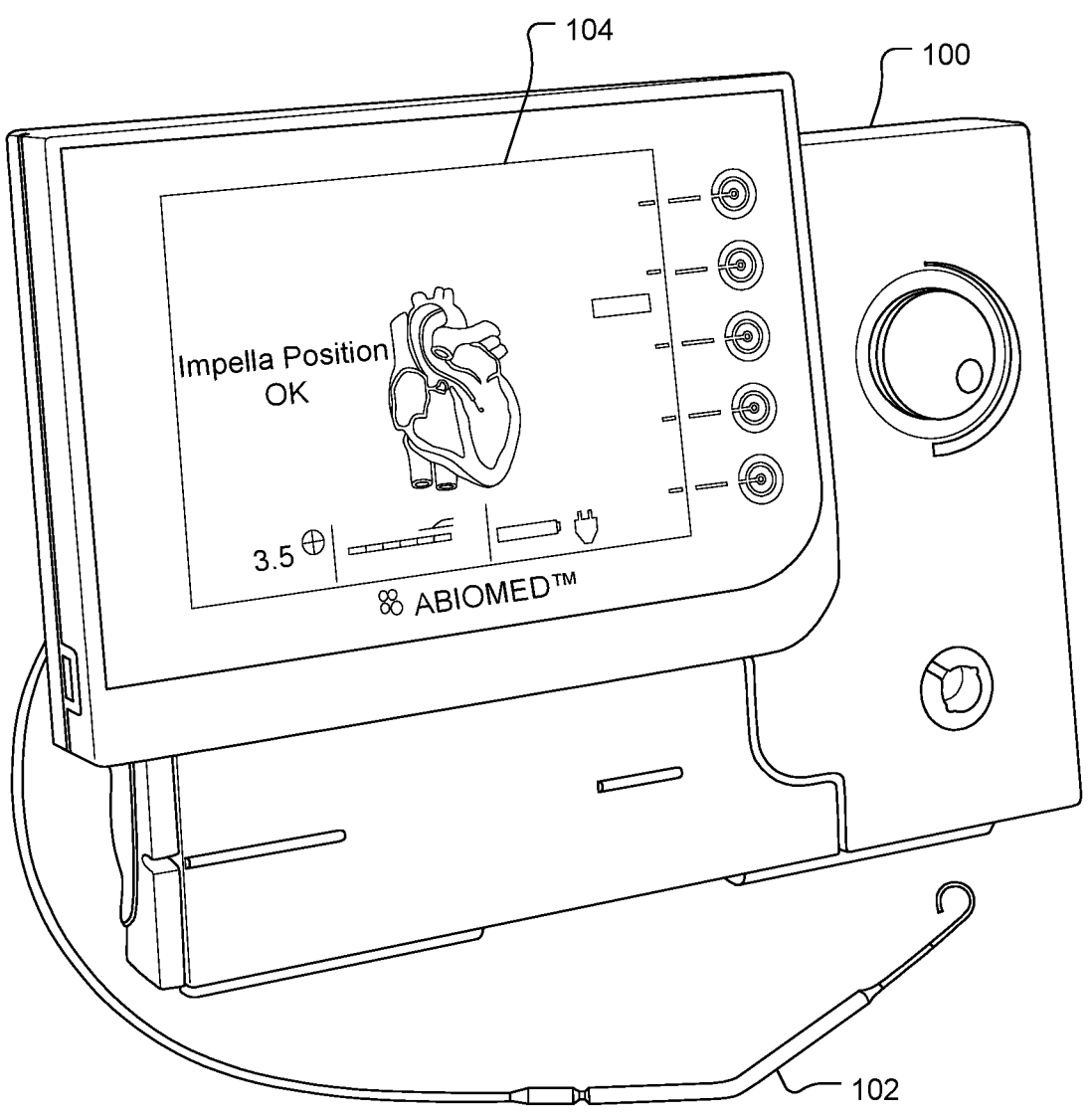
FIG. 1 is a perspective view of an exemplary convention medical device controller and an exemplary conventional medical device, in this example a heart pump, coupled to the medical device controller, according to the prior art.

FIG. 1 is a perspective view of an exemplary convention medical device controller 100 and an exemplary conventional medical device 102, in this example a heart pump, coupled to the medical device controller 100. In the example shown in FIG. 1, the medical device controller 100 is an Automated Impella Controller® from Abiomed, Inc., Danvers, MA, and the heart pump 102 is an Impella® 2.5 heart pump, also available from Abiomed, Inc., although any suitable medical device and controller may be used. In some cases, the medical device and its associated medical device controller are combined. Such a combination is referred to herein simply as a medical device controller.

The medical device controller 100 includes a display screen 104, on which the medical device controller 100 displays operational data about the medical device 102, such as heart signal level, battery temperature, blood flow rate and plumbing integrity. As discussed in more detail herein, the medical device controller 100 may be connected to a computer network and thereby send images of contents displayed on the screen 104 to a remote server (not shown).

Figure 2:
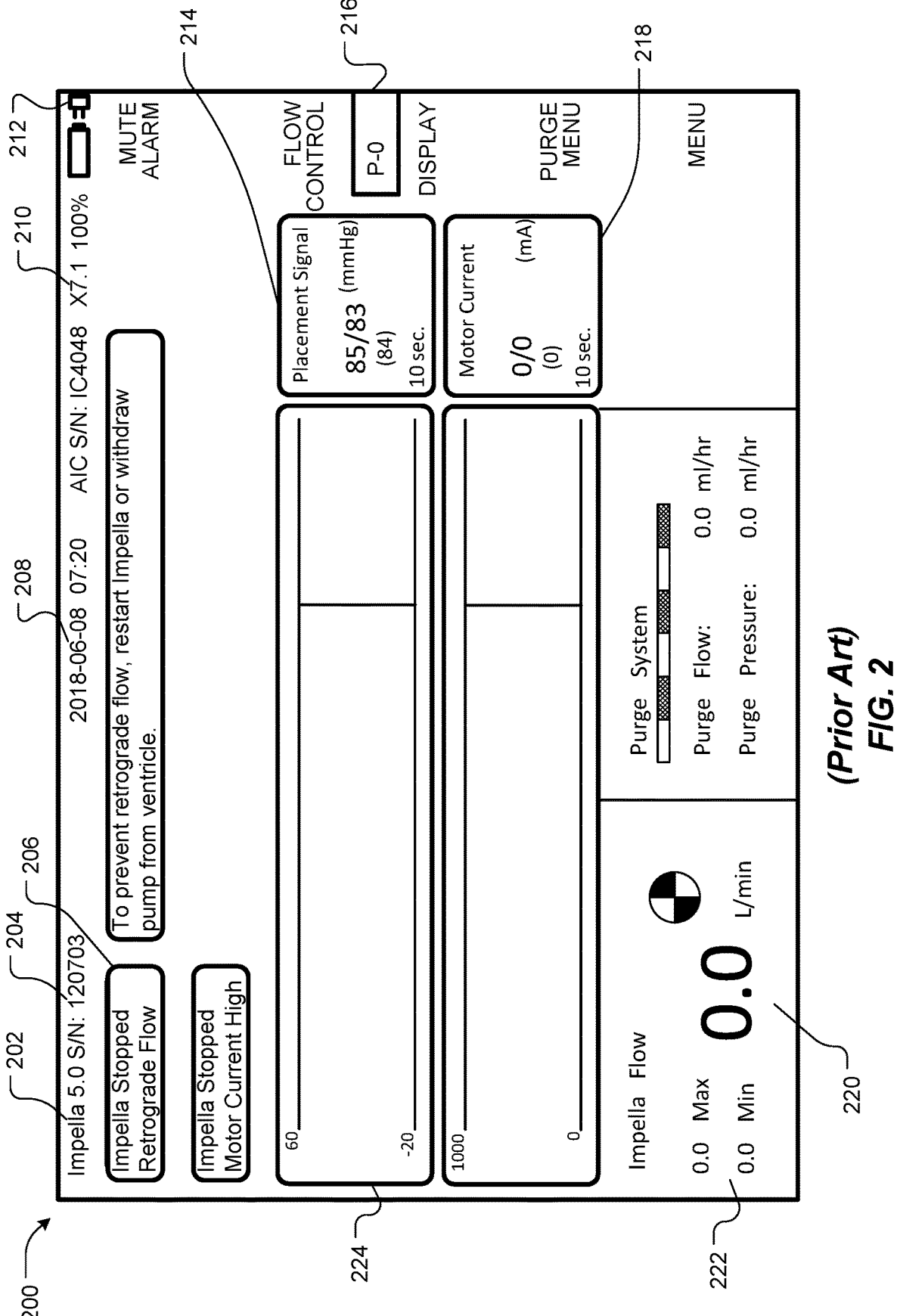
FIG. 2 shows exemplary hypothetical display screen contents that may be displayed on a screen of the medical device controller of FIG. 1, according to the prior art.

FIG. 2 shows exemplary hypothetical display screen contents 200 that may be displayed on the screen 104 of the medical device controller 100 of FIG. 1. For example, the display screen contents may include a heart pump type ("Impella 5.0") 202, a heart pump serial number ("120703") 204, a warning/error message 206, date and time 208, controller software version number 210, power source icon 212, a placement signal 214, a present heart pump speed (performance) setting ("P-0") 216, a heart pump motor current value 218, a current or average blood flow rate 220 and minimum and maximum blood flow rates 222, as well as various graphs 224. The display screen contents 200 are typically pixelated.

Major Components

Figure 3:
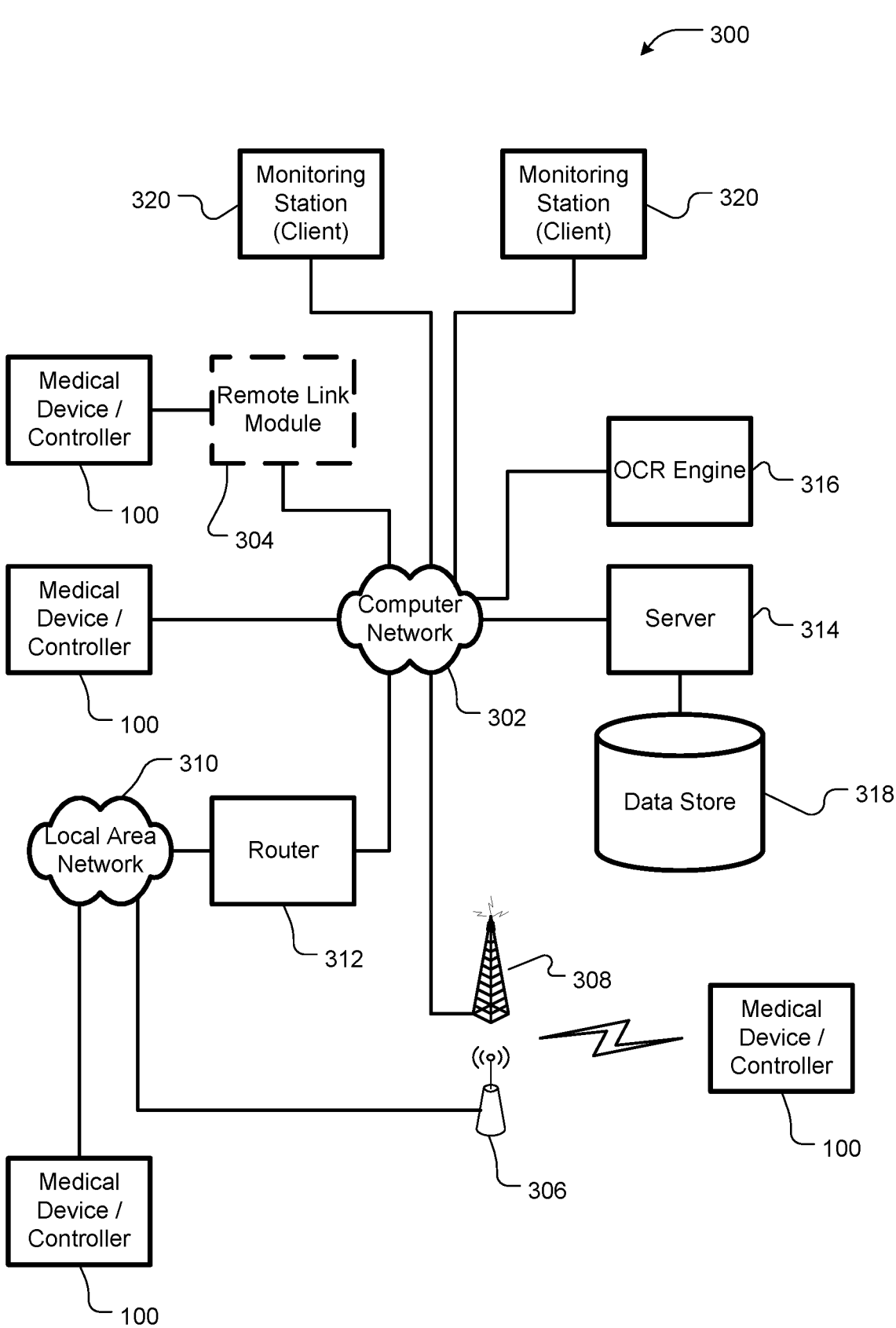
FIG. 3 is a schematic block diagram of major components of a medical device location and tracking system for locating and tracking medical device controllers, such as the medical device controller of FIGS. 1 and 2, according to an embodiment of the present invention.

FIG. 3 is a schematic diagram of major components of a medical device location and tracking system 300. The system 300 may collect, store and retrieve operational data from and about a plurality of medical device controllers 100. In addition, the system 300 locates and tracks locations of the medical device controllers 100, as each medical device controller 100 is moved from one physical location to another.

For simplicity, only medical device controllers 100, and not separate medical devices, are shown in FIG. 3. Although only four medical device controllers 100 are shown, other numbers of medical device controllers 100 may be used. Each medical device controller 100 is connectable to a computer network 302, optionally via a remote link module 304. The computer network 302 may include wired and/or wireless segments and/or networks, such as wireless networks that conform to an IEEE 802.11x standard (wireless local area networks (WLANs), commonly referred to as "Wi-Fi"), represented by a wireless access point 306, and/or cellular networks, represented by a cell site 308. The computer network 302 may include private and/or public networks, such as a local area network (LAN) 310, such as an Ethernet network, connected via a router 312, and/or metropolitan area networks (MANs) and/or wide area networks (WANs), such as the Internet (not shown).

Each medical device controller 100 is configured to automatically repeatedly capture status information about the medical device connected thereto and display the status information on a display screen 104 (FIG. 1). As noted, FIG. 2 shows respective hypothetical display screen contents 200 that may be displayed on the screen 104 of any given medical device controller 100.

A server 314 is configured to automatically periodically or occasionally request and receive an image of the contents displayed on the screen 104 of each medical device controller 100, typically about every 20 seconds. The request and the image are sent via the computer network 302. The image may be sent in one or more messages encoded as a video frame or a sequence of video frames. The video frame(s) may, for example, contain pixelated copies of images displayed on the display screens 104 of the medical device controllers 100.

The server 314 is configured to process the received frames (images). The server 314 parses the images and extracts textual information, such as heart pump serial number, blood flow rate, warning message text and the like, by optical character recognizing (OCR) portions of the images. The server 314 may also parse the images and extract graphical information, such as a power source icon, and compare this graphical information to predetermined pixel patterns and/or colors. The server 314 may include an OCR engine, or the server 314 may communicate with an external OCR engine 316, such as via the computer network 302. The server 314 may then use the recognized text to automatically ascertain serial numbers or other identifiers of the medical device controllers 100, operating parameters of the medical device controllers 100, whether an alarm has been raised by one of the medical device controllers 100, etc.

A data store 318 is configured to store one or more media files, and in particular frames (images), such as MP4 video or other suitable types of media files, and the server 314 is configured to automatically store received frames (images) in the data store 318. The data store 318 records the screen images received by the server 314 for later playback, such as in response to requests from one of several monitoring stations 320. Only two monitoring stations 320 are shown for simplicity, however any number of monitoring stations 320 may be included. The monitoring stations 320 may use cloud-based technology to securely and remotely display images of the medical device controller 100 screens 104 to physicians and hospital staff anywhere with Internet connectivity. An exemplary remote monitoring system is available under the trade name Impella Connect® online device management system, available from Abiomed, Inc., Danvers, MA.

The data store 318 is configured to provide a requested portion of the stored media file in response to a provision request. The data store 318 thereby supports playback of the medical device controller 100 status information. For example, the data store 318 may provide one or more frames (images) of video stored in the media file, for display by a monitoring station 320 to a user. The server 314 may also be configured to provide status information about one or more of the medical device controllers 100 to ones of the monitoring stations 320, based on images received by the server 314 in real time and/or based on historical information held in the data store 318.

Each monitoring station 320 may display information about a plurality of medical device controllers 100, including their respective physical locations. As noted, each medical device controller 100 may be moved from one physical location to another, which poses a problem for the medical personnel who view the monitoring stations 320, if the location information is missing or inaccurate. For example, a user of a monitoring station 320 may command the monitoring station 320 to display information about all medical device controllers 100 within a specified location. However, if location information is missing or incorrect for one or more of the medical device controllers 100, information about a wrong set of medical device controllers 100 will be displayed to the user.

Automatic Physical Location Inference

Figure 4:
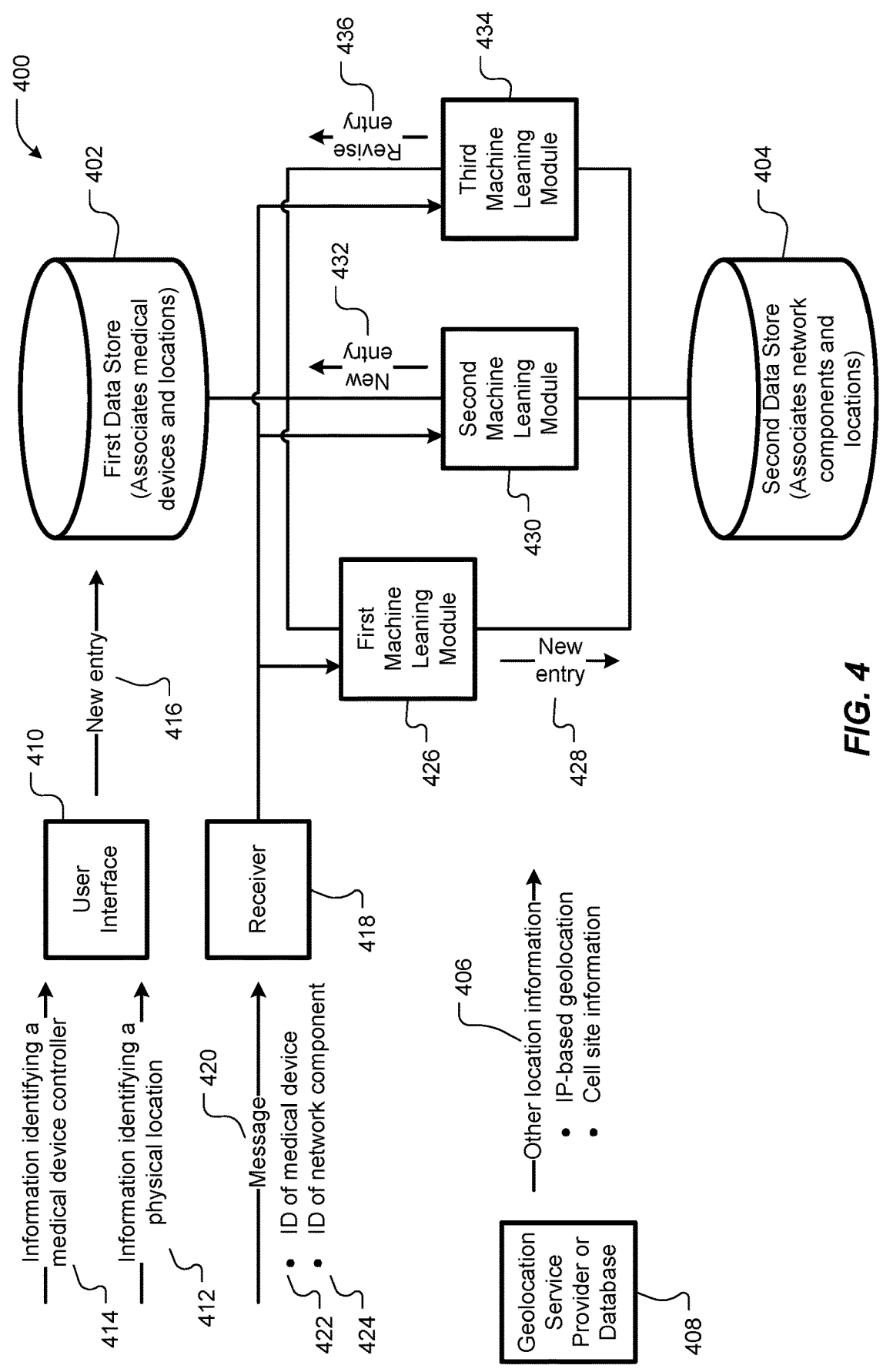
FIG. 4 is a diagram schematically illustrating components of a server of FIG. 3 and operations performed by the server, according to an embodiment of the present invention.

To solve this problem, the server 314 includes components 400 shown schematically in FIG. 4. Using these components 400, the server 314 automatically learns physical locations of some or all of the medical device controllers 100 and automatically tracks changes in these physical locations. This process may begin with a user manually entering physical location information about a subset, such as one or more, of the medical device controllers 100. This information is stored in a first data store 402, which associates medical device controllers 100 with their respective physical locations. This process is referred to as seeding the first data store 402.

From this information, the server 314 infers physical locations of components of the computer network 302. For example, if the server 314 communicates via the computer network 302 with a medical device controller 100 whose physical location is known, and the communication involves a network component, such as a wireless access point 306 (FIG. 3), that is necessarily proximate the medical device controller 100, the server 314 stores information in a second data store 404, which associates network components with their respective physical locations.

Necessarily proximate does not require any specific proximity. The server 314 may use whatever information is available, and the server 314 may replace known physical location information with more accurate physical location information, as the more accurate physical location information becomes available. For example, the server 314 may initially store physical location information about an Internet protocol (IP) address, such as a physical location associated with an IP network to which the medical device controller 100 is connected, and then later replace that location information with more accurate physical location information about a wireless access point.

From the physical location information about network components, the server 314 infers physical locations of medical device controllers 100 whose locations are not yet known, or whose physical locations change from their previously known values. For example, if the server 314 communicates with a medical device controller 100 whose physical location is unknown, but the communication involves a network component that is necessarily proximate the medical device controller 100 and the location of the network component is known, the server 314 automatically infers the physical location of the medical device controller 100 from the physical location of the network component.

Similarly, if the server 314 communicates with a medical device controller 100 whose physical location is known, but the communication involves a network component that is necessarily proximate the medical device controller 100 and the location of the network component is known with more precision than the physical location of the medical device controller 100, the server 314 automatically infers a more precise physical location of the medical device controller 100 from the physical location of the network component and the server 314 updates the physical location of the medical device controller 100.

Similarly, if the server 314 communicates with a medical device controller 100 whose physical location is known, and the communication involves a network component that is necessarily proximate the medical device controller 100 and the location of the network component is known, but the network component's known location does not match the known location of the medical device controller 100, the server 314 automatically infers the medical device controller 100 has been moved to a new physical location, and the server 314 infers the new physical location from the physical location of the network component.

The server 314 may use other sources of physical location information 406. For example, several commercial vendors provide IP-based geolocation information, which includes physical locations associated with IP addresses. The server 314 may use the IP address, or a portion thereof, from a network message from a medical device controller 100 to automatically ascertain, or at least estimate, the physical location of the medical device controller 100, or at least the address of an Internet service provider (ISP) who handles network traffic from the medical device controller 100, by querying such an IP-based geolocation service or database 408. The well-known Whois Database may be similarly used. Databases of cell sites may be similarly used. Thus, optionally or alternatively, the first and/or second data store 402 and/or 404 may be seeded with information from one or more geolocation service providers or databases 408.

Figure 5A:
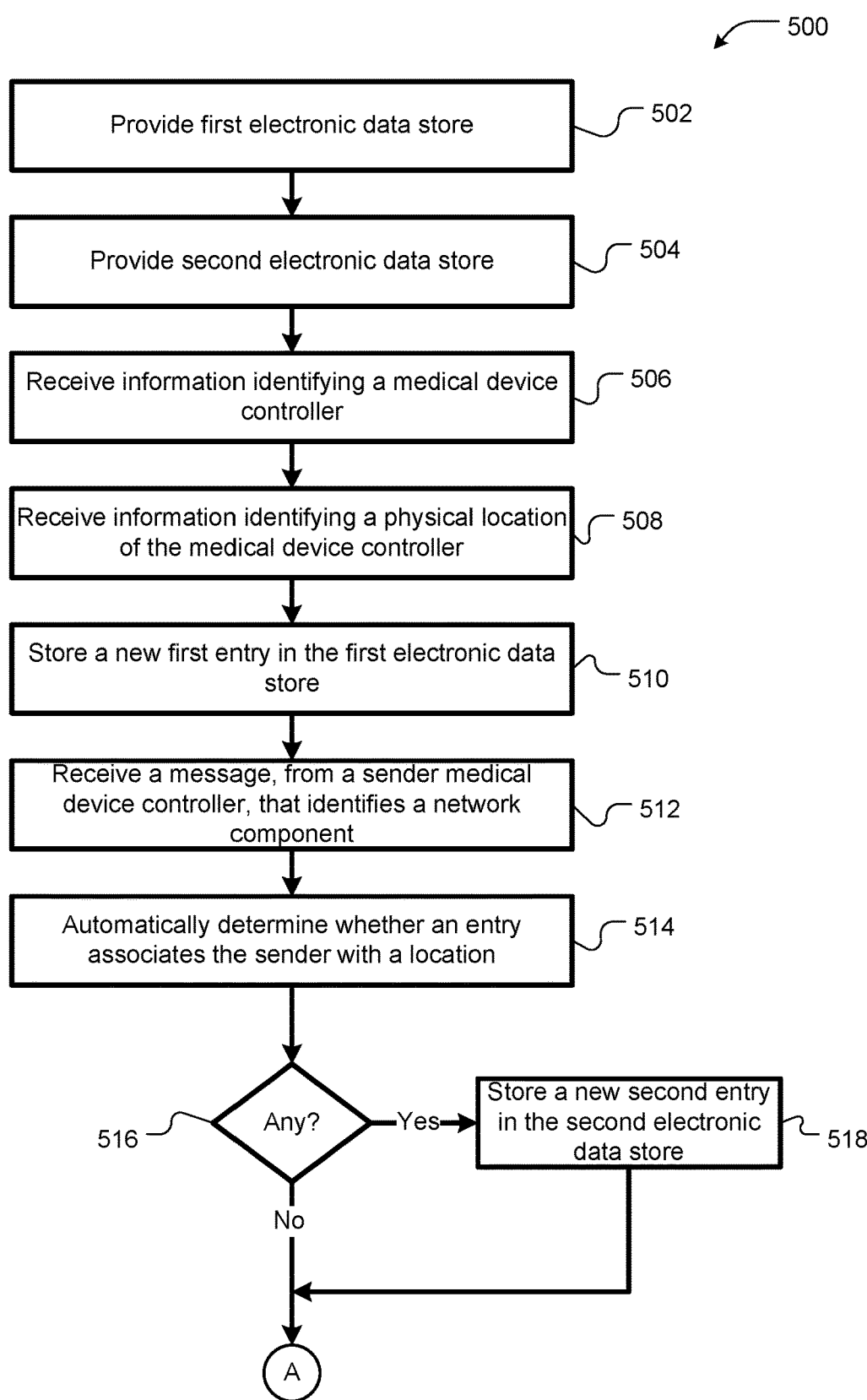
FIGS. 5A-5C (collectively, FIG. 5) form a flowchart schematically illustrating operations performed by the server components of FIG. 4, including operations performed by a first machine learning module (FIG. 5A), operations performed by a second machine learning module (FIG. 5B) and operations performed by a third machine learning module (FIG. 5C), according to respective embodiments of the present invention.
Figure 5B:
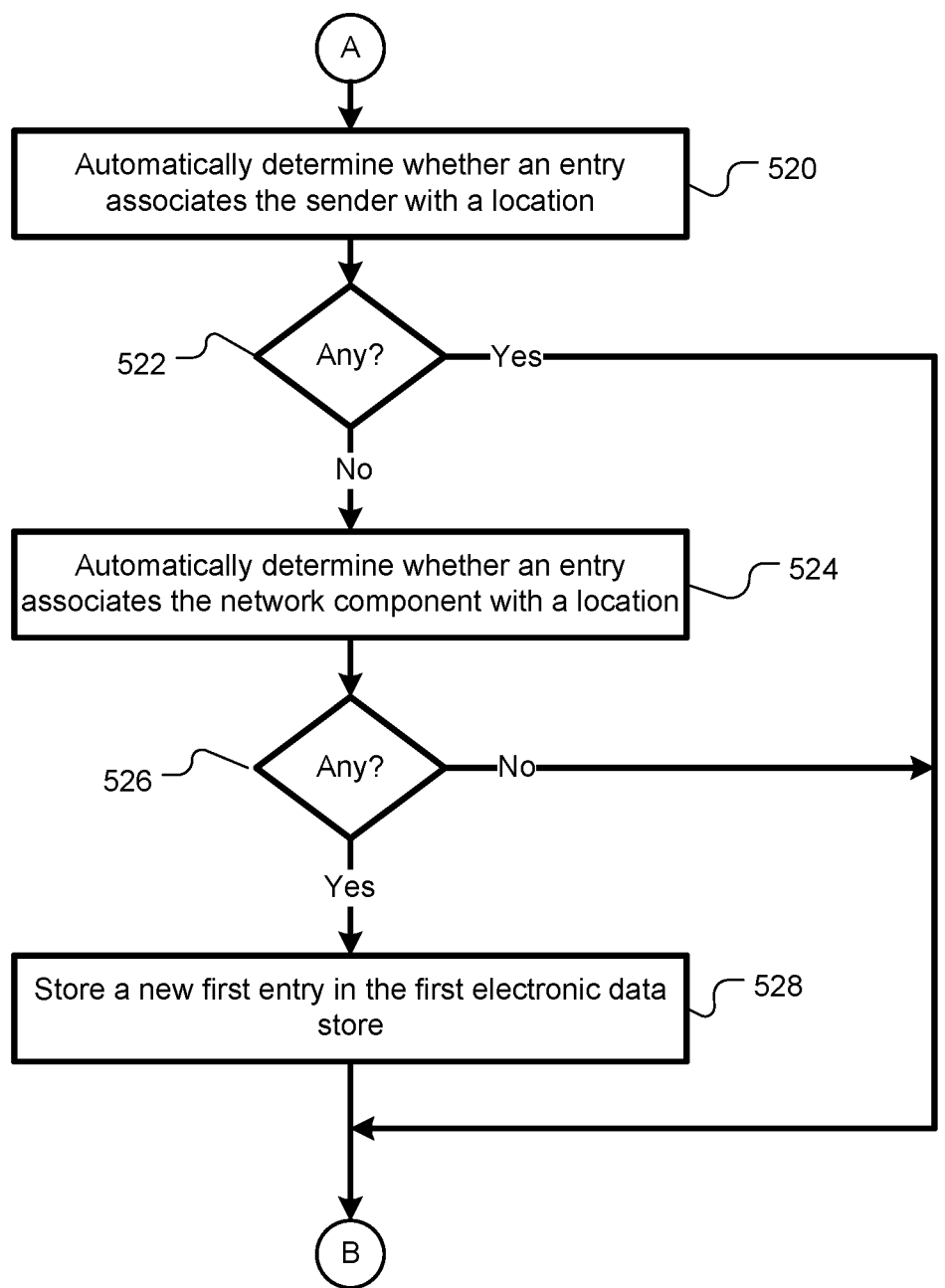
Figure 5C:
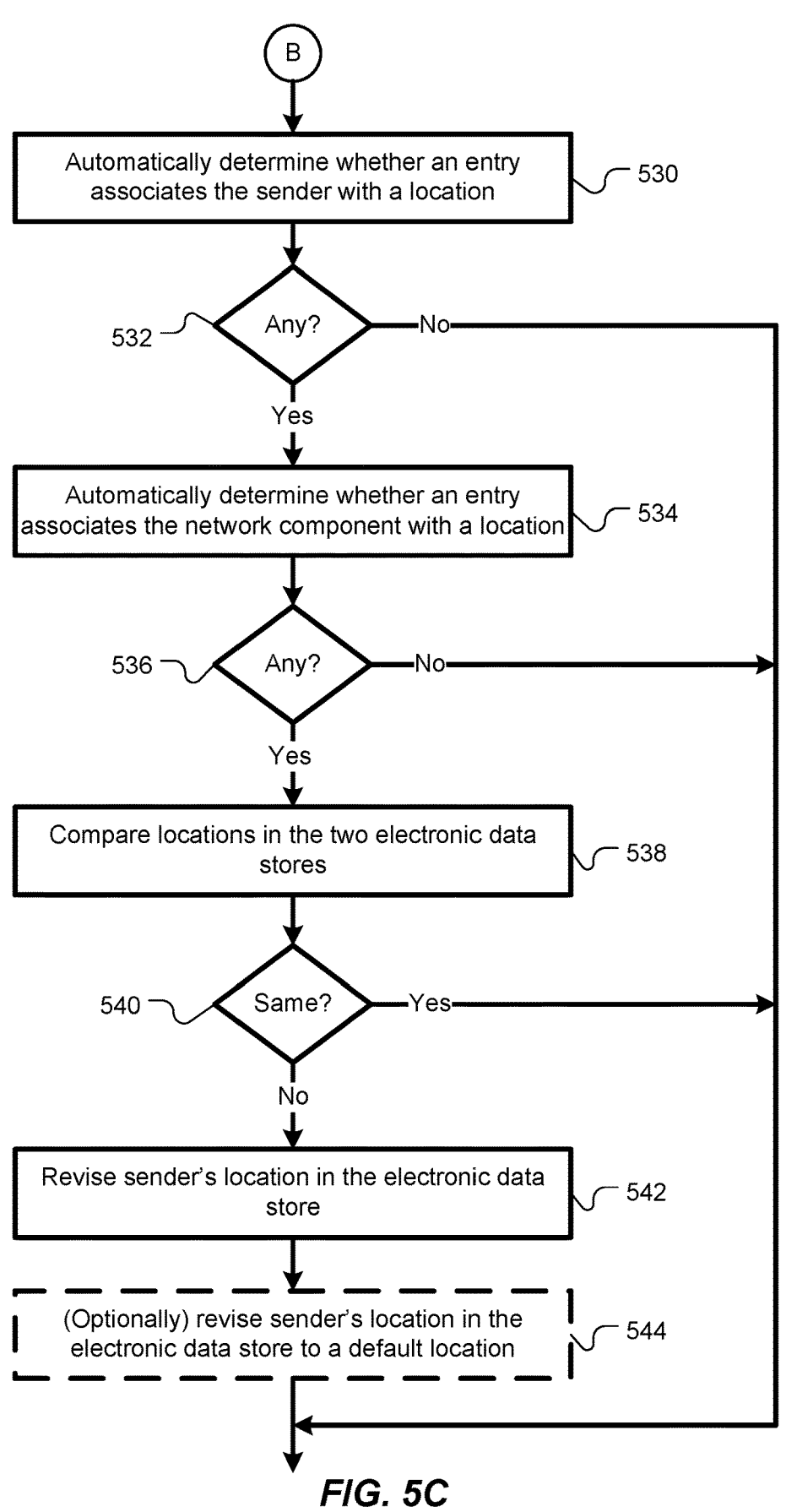

FIG. 5 is a flowchart schematically illustrating operations performed by the server 314 to implement a method 500 for locating and tracking medical devices. At 502, the first electronic data store 402 is provided. The first data store 402 is configured to store a plurality of first entries. Each first entry contains information that associates a respective medical device controller 100 with a respective physical location. Table 1 lists exemplary hypothetical contents of the first data store 402, according to an embodiment of the present invention. The left column lists identifiers of medical device controllers 100, such as serial numbers. The right column lists identifiers of physical locations associated with the respective medical device controllers 100 in the left column.

TABLE 1

| Information associating medical device controllers with physical locations | |
|---|---|
| Medical device controller | Physical location |
| Controller ID 1 | Location 1 |
| Controller ID 2 | Location 2 |
| Controller ID 4 | Location 1 |
| Controller ID 5 | Location 7 |
| . . . | . . . |

At 504 (FIG. 5), the second electronic data store 404 is provided. The second data store 404 is configured to store a plurality of second entries. Each second entry contains information that associates a respective computer network component with a respective physical location. Table 2 lists exemplary hypothetical contents of the second data store 404, according to an embodiment of the present invention. The left column lists identifiers of network components, such as IP or media access control (MAC) addresses of networks or routers (such as local area network 310 or router 312), service set identifiers (SSIDs) of wireless access points (such as wireless access point 306), GSM cell identifiers (CIDs) of base transceiver stations (BTSs) or sector of a BTS. The right column lists identifiers of physical locations associated with the respective network components in the left column.

TABLE 1

| Information associating computer network components with physical locations | |
|---|---|
| Computer network component | Physical location |
| Component ID 1 | Location 2 |
| Component ID 2 | Location 5 |

TABLE 1-continued

| Information associating computer network components with physical locations | |
|---|---|
| Computer network component | Physical location |
| Component ID 3 | Location 3 |
| Component ID 5 | Location 1 |
| . . . | . . . |

At 506 (FIG. 5), information identifying a medical device controller (an "identified medical device controller") is received, and at 508, information identifying a physical location (an "entered physical location") of the identified medical device is received. As noted, the first data store 402 may be seeded through one or more user entries. The server 314 (FIG. 3) may include a user interface 410 (FIG. 4), through which a user may enter information identifying a physical location of a medical device controller 100 and, optionally, information identifying the medical device controller 100.

Figure 6:
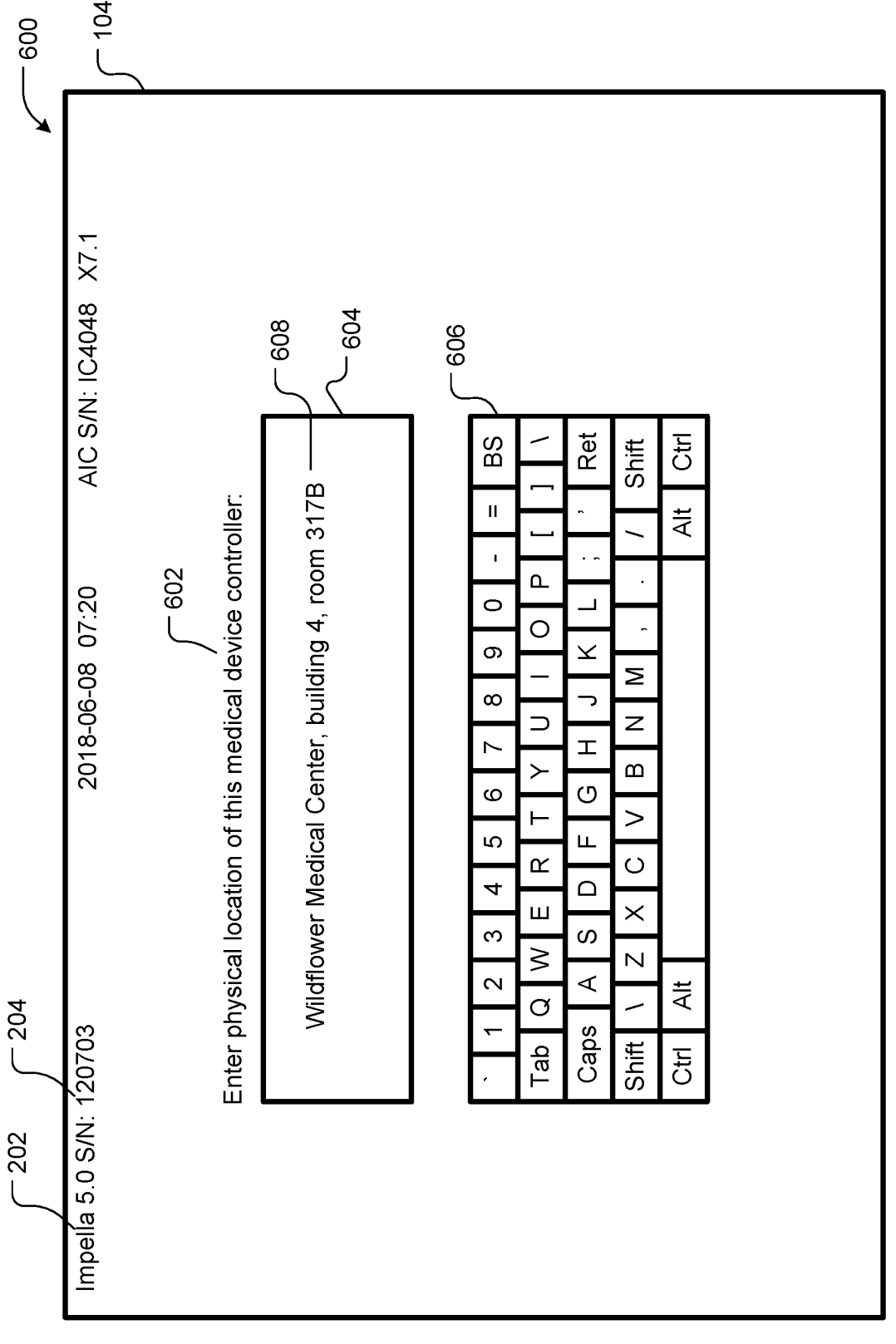
FIG. 6 shows an exemplary hypothetical user interface displayed on the display screen that may be implemented by a medical device controller of FIG. 1 to provide medical device location information to the server of FIGS. 3-5, according to an embodiment of the present invention.

One embodiment of such a user interface 410 is implemented by the medical device controller 100. FIG. 6 shows an exemplary user interface 600 displayed on the display screen 104 of a medical device controller 100. In this embodiment, the display screen 104 is a touch-sensitive screen capable of receiving user inputs, although in other embodiments a physical keyboard may be connected to the medical device controller 100. The user interface 600 includes a prompt 602 and an area 604 in which the user can enter text that identifies the physical location of the medical device controller 100. The user interface 600 includes a virtual keyboard 606 on the touch-sensitive display screen 104, on which the user can make the entry. A hypothetical entry is shown at 608. The user's input constitutes information identifying a physical location 412 (FIG. 4) entered into the user interface 410.

The user need not enter information identifying the medical device controller 100, because the medical device controller 100 already stores information, such as its serial number, as shown on the display screen 104 at 204. When the medical device controller 100 sends the user's input 608 to the server 314, the medical device controller 100 also sends its serial number or other identifying information. The serial number or other identifying information constitutes information identifying a medical device controller 414 (FIG. 4).

Figure 7:
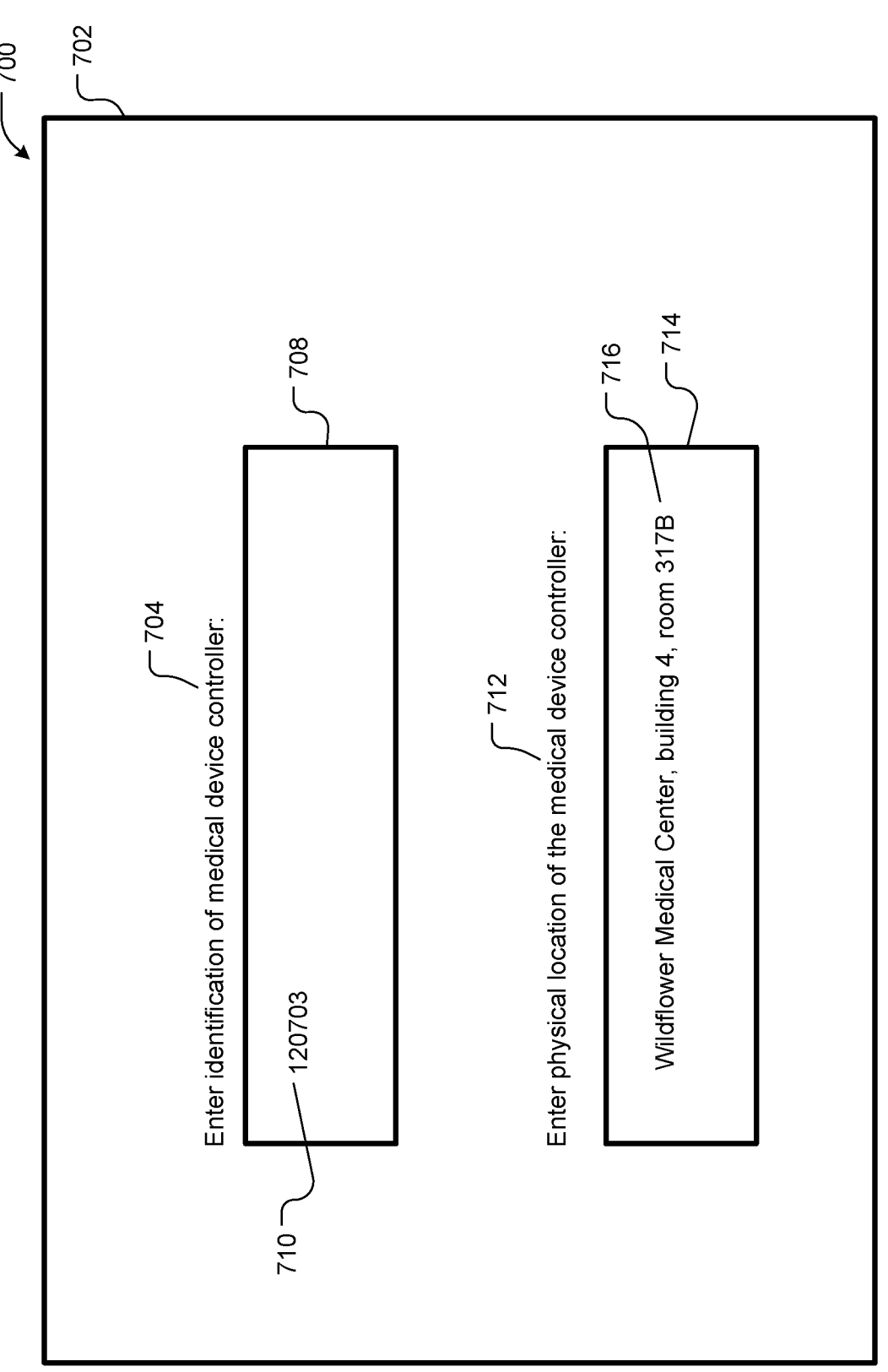
FIG. 7 shows an exemplary hypothetical user interface displayed on a display screen that may be implemented by a monitoring station of FIG. 1 to provide medical device location information to the server of FIGS. 3-5, according to an embodiment of the present invention.

In another embodiment, the user interface 410 is implemented by one of the monitoring stations 320 (FIG. 3). FIG. 7 shows an exemplary user interface 700 displayed on a display screen 702 of the monitoring station 320. In this embodiment, the display screen 702 may be a touch-sensitive screen, as in the user interface 600 described with reference to FIG. 6. Optionally or alternatively, a physical keyboard may be connected to the monitoring station 320. The user interface 700 includes a prompt 704 and an area 708 in which the user can enter text that identifies the medical device controller 100, such as the serial number 710 of the medical device controller 100. The user interface 700 also includes a prompt 712 and an area 714 in which the user can enter text that identifies the physical location of the medical device controller 100. A hypothetical entry is shown at 716. The user entries 710 and 716 constitute the information identifying a medical device controller 414 (FIG. 4) and the information identifying a physical location 412.

In yet another embodiment, the user interface 410 is implemented through an administrative console (not shown)

communicatively coupled to the server 314. This administrative console may be implemented by a physical or virtual display and keyboard, a telnet connection from another computer or any other suitable interface.

Based on the information the user interface 410 collects, i.e., the information 414 identifying the medical device controller 100 and the information 412 identifying a physical location, the user interface 410 stores a new first entry 416 in the first electronic data store 402, as indicated by operation 510 (FIG. 5). The new first entry associates the identified medical device controller 100 with the entered physical location, as discussed with respect to Table 1.

As noted, the medical device controllers 100 send messages to the server 314 via the computer network 302 to convey images of the display screens 104 on the medical device controllers 100. These messages include "from" addresses that identify the respective medical device controllers 100. The medical device controllers 100 may send additional messages to the server 314 via the computer network 302. These additional messages may contain information about a network environment the medical device controllers 100 sense. From this information, the server 314 can infer which network component(s) is (are) proximate the medical device controller 100. The server 314 includes a receiver 418 (FIG. 4) configured to receive these network messages 420.

For example, if a medical device controller 100 is capable of wireless network communication, the medical device controller 100 sends information, such as SSIDs, to the server 314 identifying wireless access points 306 or other wireless infrastructure that is within radio range of the medical device controller 100 and with which the medical device controller 100 can wirelessly communicate. Optionally, this information includes relative or absolute received signal strength indicators (RSSIs), as measured by the medical device controller 100, for the in-range wireless access points 306 or other wireless infrastructure. Based on the RSSIs, the server 314 can infer relative proximity of the identified wireless access points 306 to the medical device controller 100, such as based on relative strengths of signals from the various wireless access points 306, etc.

In other examples, the medical device controller 100 sends messages to the server 314 identifying other network components, such as routers, switches, etc., with which the medical device controller 100 has communicated. The medical device controller 100 may use tools, such as traceroute, ping, etc. to probe its network environment and automatically determine relative proximity of the network components to the medical device controller 100. The medical device controller can then send this proximity information, and identifiers of the respective network components, to the server 314.

Thus, any message received by the server 314 may include information 422 (FIG. 4) identifying a sender medical device controller 100 and information 424 identifying a computer network component. This operation is summarized at operation 512 (FIG. 5), where the server 314 receives, via the computer network 302 a message 420 from a sender medical device controller 100. The message includes: (a) an identifier 422 of the sender medical device controller 100 and (b) an identifier 424 of a computer network component.

First Machine Learning Module Infers Location of a Network Component

At 514 (FIG. 5), in response to receipt of the message 420, the server 314 automatically determines whether an entry in the first electronic data store 402 associates the sender medical device controller 100 with a respective physical location. This test determines whether the first electronic data store 402 contains such an association, not whether the sender medical device controller 100 is associated with a particular physical location. At 516, if an entry in the first electronic data store 402 is found that associates the sender medical device controller 100 with a respective physical location, control passes to 518, where a first machine learning module 426 in the server 314 stores a new second entry 428 in the second electronic data store 404. The new second entry 428 associates the computer network component with the physical location associated with the sender medical device controller 100, as discussed with respect to Table 2.

The identifier 424 of the computer network device may identify a computer network component with which the sender medical device controller 100 has communicated, or with which the sender medical device controller 100 has directly communicated wirelessly. For example, the identifier 424 of the computer network device may identify a wireless access point 306 (FIG. 3), with which the sender medical device controller 100 has directly communicated wirelessly, or a base station identifier of a cellular base station 308, with which the sender medical device controller 100 has directly communicated wirelessly. The identifier 424 of the computer network component may identify a computer network component, through which the message 420 traveled en route to the receiver 418. The identifier 424 of the computer network component may, for example, include an IP address or a MAC address.

Second Machine Learning Module Infers Location of a Medical Device Controller The server 324 may include a second machine learning module 430 (FIG. 4). The second machine learning module 430 may be configured, in response to receipt of the message 420, to automatically determine whether an entry in the first electronic data store 402 associates the sender medical device controller 100 (identified by ID 422) with a respective physical location, as indicated by operation 520 (FIG. 5).

If no entry in the first electronic data store 402 is found that associates the sender medical device controller 100 with a respective physical location, control passes from operation 522 to operation 524, where the server 314 determines whether an entry in the second electronic data store 404 associates the computer network component (identified by ID 424) with a respective physical location. If no entry in the first electronic data store 402 is found that associates the sender medical device controller 100 with a respective physical location and, at operation 524, an entry in the second electronic data store 404 is found that associates the computer network component with a respective physical location, control passes from operation 526 to operation 528, where the second machine learning module 430 stores a new first entry 432 in the first electronic data store 402. The new first entry 432 associates the sender medical device controller 100 (identified by ID 422) with the physical location associated with the computer network component (identified by ID 424). The location of the computer network component is copied from the second data store 404, as represented by the right column in Table 2.

Third Machine Leaning Module Infers Movement of a Medical Device Controller

The server 324 may include a third machine learning module 434 (FIG. 4). The third machine learning module 434 may be configured, in response to receipt of the message 420, to automatically determine whether an entry in the first electronic data store 402 associates the sender medical device controller 100 (identified by ID 422) with a respective physical location, as indicated by operation 530. If an entry in the first electronic data store 402 is found that associates the sender medical device controller 100 with a respective physical location, control passes from operation 532 to operation 534, where the server 314 determines whether an entry in the second electronic data store 404 associates the computer network component (identified by ID 424) with a respective physical location.

If an entry in the first electronic data store 402 is found that associates the sender medical device controller 100 with a respective physical location and, at operation 534, an entry in the second electronic data store 404 is found that associates the computer network component with a respective physical location, control passes from operation 536 to operation 538. At operation 538, the server compares the physical location associated with the sender medical device controller 100 in the first electronic data store 402 to the physical location associated with the computer network device in the second electronic data store 404.

If an entry in the first electronic data store 402 is found that associates the sender medical device controller 100 with a respective physical location and an entry in the second electronic data store 404 is found that associates the computer network device with a respective physical location and, at operation 540, the physical location associated with the sender medical device controller 100 in the first electronic data store 402 is found to differ from the physical location associated with the computer network device in the second electronic data store 404, at operation 542 the server revises the entry 436 (FIG. 4) in the first electronic data store 402 to associate the sender medical device controller 100 with the physical location associated with the computer network device in the second electronic data store 404.

In some embodiments, at operation 542, the server only temporarily revises the entry 436 (FIG. 4) in the first electronic data store 402 to associate the sender medical device controller 100 with the physical location associated with the computer network device in the second electronic data store 404. Subsequently, such as after a predetermined time, the server revises the entry 436 (FIG. 4) in the first electronic data store 402 to associate the sender medical device controller 100 with a default location, as indicated at operation 544.

In any embodiment, the third machine learning module may be configured to temporarily revise the entry in the first electronic data store to associate the sender medical device controller with the physical location associated with the computer network device in the second electronic data store. The third machine learning module may be further configured to automatically subsequently revise the entry in the first electronic data store to associate the sender medical device controller with a default value.

The server 314, including the first, second and third machine learning modules 426, 430 and 434 and the receiver 418, may be implemented by a processor executing instructions stored in a memory. The instructions may include instructions for implementing the method 500 described with reference to FIG. 5, as well as processes to implement the user interfaces described with reference to FIGS. 6 and 7.

The first and second data stores 402 and 404 may be implemented with a relational database and may include a front end (load balancer) that distributes access requests across multiple copies of the database to support a high volume of requests.

In the written description and in the claims, a phrase such as "automatically determine whether an entry in the first electronic data store associates the sender medical device controller (or the network component) with a respective physical location" means determine whether the electronic data store contains such an association, not whether the sender medical device controller (or the network component, as the case may be) is associated with a particular physical location. In such a phrase, "a respective physical location" does not mean a particular physical location, it means any physical location. Thus, the determination does not make a comparison to a particular physical location. Instead, the determination merely tests whether an association currently exists.

Consequently, if the data store contains information documenting such an association, a result of the determination is TRUE, whereas if the data store does not contain information documenting any such association, the result of the determination is FALSE. The result of the determination may be referenced in a subsequent phrase, such as "if an entry in the electronic data store is found that associates the sender medical device controller (or the network component, as the case may be) with a respective physical location, . . . " In such a phrase, "a respective physical location" does not create an antecedent basis or clarity problem, because no particular physical location is being referred to. This phrase is equivalent to "if the previous determination produced a result of TRUE, . . . ."

While the invention is described through the above-described exemplary embodiments, modifications to, and variations of, the illustrated embodiments may be made without departing from the inventive concepts disclosed herein. For example, although specific network component identifiers, such as IP addresses and SSIDs, may be recited in relation to disclosed embodiments, within the scope of the invention, the values of all parameters may vary over wide ranges to suit different applications.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The server 314, including the first, second and third machine learning modules 426, 430 and 434, the receiver 418, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective elements from one another and are not intended to indicate any particular order or total number of elements in any particular embodiment. Thus, for example, a given embodiment may include only a second machine learning module and a third machine learning module.

What is claimed is:

1. A medical device controller location and tracking system, the system comprising:

a first electronic data store comprising a plurality of first entries, wherein each first entry contains information that associates a medical device controller with a physical location;

a second electronic data store comprising a plurality of second entries, wherein each second entry contains information that associates a computer network device with a physical location;

a plurality of medical device controllers, wherein each medical device controller comprises a user interface configured to receive information, from a human user, identifying an entered physical location of the respective medical device controller, and wherein each user interface comprises a display screen configured to display operational data for a heart pump communicatively coupled to the respective medical device controller;

a plurality of computer network devices;

a monitoring station configured to display physical locations associated with one or more of the plurality of medical device controllers; and a server comprising a plurality of machine learning modules, the server configured to:

receive messages, via a computer network, from the plurality of medical device controllers, wherein each message includes: (a) an identifier of the respective medical device controller, (b) an identifier of one of the plurality of computer network devices through which the respective message traveled en route to the server, and (c) an image of at least some of the contents displayed on the display screen of the respective medical device controller;

for each of the received messages, learn a physical location of the respective medical device controller with the plurality of machine learning modules by:

extracting at least some of the operational data for the heart pump communicatively coupled to the respective medical device controller from the respective image;

determining whether an entry in the first electronic data store associates the respective medical device controller with a physical location;

determining whether an entry in the second electronic data store associates the respective one of the plurality of computer network devices with a physical location;

if (a) an entry in the first electronic data store is found that associates the respective medical device controller with a physical location and (b) no entry in the second electronic data store is found that associates the respective one of the plurality of computer network devices with a physical location, then storing, with the plurality of machine learning modules, a new second entry in the second electronic data store, wherein the new second entry associates the respective one of the plurality of computer network devices with the physical location associated with the respective medical device controller in the first electronic data store;

if (a) no entry in the first electronic data store is found that associates the respective medical device controller with a physical location and (b) an entry in the second electronic data store is found that associates the respective one of the plurality of computer network devices with a physical location, then storing, with the plurality of machine learning modules, a new first entry in the first electronic data store, wherein the new first entry associates the respective medical device controller with the physical location associated with the respective one of the plurality of computer network devices in the second electronic data store; and if (a) an entry in the first electronic data store is found that associates the respective medical device controller with a physical location, (b) an entry in the second electronic data store is found that associates the respective one of the plurality of computer network devices with a physical location, and (c) a comparison indicates that the physical location associated with the respective medical device controller in the first electronic data store differs from the physical location associated with the respective one of the plurality of computer network devices in the second electronic data store, then revising, with the plurality of machine learning modules, the entry in the first electronic data store to associate the respective medical device controller with the physical location associated with the respective one of the plurality of computer network devices in the second electronic data store;

transmit, via the computer network, to the monitoring station, a physical location of one of the plurality of medical device controllers that was learned by the plurality of machine learning modules; and transmit, via the computer network, to the monitoring station, an alarm based on the operational data extracted from one of the received messages, wherein the one received message was received from the one medical device controller, and wherein the alarm prompts an adjustment to a speed setting or a motor current value of the heart pump communicatively coupled to the one medical device controller.

2. The system of claim 1, wherein, for each received message, the identifier of the respective medical device controller comprises a serial number, and wherein, for each of the received messages, the server is further configured to extract the serial number from the respective image.

3. The system of claim 2, wherein, for each received message, the identifier of the respective one of the plurality of computer network devices comprises an Internet protocol (IP) address, a media access control (MAC) addresses, or a service set identifier (SSID).

4. The system of claim 1, wherein at least one of the plurality of first entries in the first electronic data store was created in response to a human user providing a physical location of one of the plurality of medical device controllers through the user interface of that medical device controller.

5. The system of claim 1, wherein, for each received message, the respective image comprises a serial number, a placement signal, a speed setting, a motor current value, a blood flow rate, and one or more graphs.

6. The system of claim 5, wherein the respective image of the one received message further comprises an error message.

7. The system of claim 1, wherein the operational data extracted from the one received message comprises a heart signal level, a battery temperature, a blood flow rate, or an indication of plumbing integrity.

8. The system of claim 1, wherein the alarm prompts an adjustment to the speed setting of the heart pump communicatively coupled to the one medical device controller.

9. The system of claim 1, wherein the alarm prompts an adjustment to the motor current value of the heart pump communicatively coupled to the one medical device controller.

10. The system of claim 1, wherein the alarm further prompts an adjustment to a position of the heart pump communicatively coupled to the one medical device controller.

11. The system of claim 1, wherein the alarm further prompts a restart of the heart pump communicatively coupled to the one medical device controller.

12. The system of claim 1, wherein the alarm further prompts a dispatch of medical personnel to the physical location of the one medical device controller that was learned by the plurality of machine learning modules.

13. A method comprising:

receiving messages, at one or more servers, via a computer network, from a plurality of medical device controllers, wherein each medical device controller comprises a user interface configured to receive information, from a human user, identifying an entered physical location of the respective medical device controller, wherein each user interface comprises a display screen configured to display operational data for a heart pump communicatively coupled to the respective medical device controller, and wherein each message includes: (a) an identifier of the respective medical device controller, (b) an identifier of one of a plurality of computer network devices through which the respective message traveled en route to the one or more servers, and (c) an image of at least some of the contents displayed on the display screen of the respective medical device controller;

for each of the received messages, extracting at least some of the operational data for the heart pump communicatively coupled to the respective medical device controller from the respective image;

for each of the received messages, learning a physical location of the respective medical device with a plurality of machine learning modules by:

determining whether an entry in a first electronic data store associates the respective medical device controller with a physical location, wherein the first electronic data store comprises a plurality of first entries, and wherein each first entry contains information that associates a medical device controller with a physical location;

determining whether an entry in a second electronic data store associates the respective one of the plurality of computer network devices with a physical location, wherein the second electronic data store comprises a plurality of second entries, and wherein each second entry contains information that associates a computer network device with a physical location;

if (a) an entry in the first electronic data store is found that associates the respective medical device controller with a physical location and (b) no entry in the second electronic data store is found that associates the respective one of the plurality of computer network devices with a physical location, then storing, with the plurality of machine learning modules, a new second entry in the second electronic data store, wherein the new second entry associates the respective one of the plurality of computer network devices with the physical location associated with the respective medical device controller in the first electronic data store;

if (a) no entry in the first electronic data store is found that associates the respective medical device controller with a physical location and (b) an entry in the second electronic data store is found that associates the respective one of the plurality of computer network devices with a physical location, then storing, with the plurality of machine learning modules, a new first entry in the first electronic data store, wherein the new first entry associates the respective medical device controller with the physical location associated with the respective one of the plurality of computer network devices in the second electronic data store; and if (a) an entry in the first electronic data store is found that associates the respective medical device controller with a physical location, (b) an entry in the second electronic data store is found that associates the respective one of the plurality of computer network devices with a physical location, and (c) a comparison indicates that the physical location associated with the respective medical device controller in the first electronic data store differs from the physical location associated with the respective one of the plurality of computer network devices in the second electronic data store, then revising, with the plurality of machine learning modules, the entry in the first electronic data store to associate the respective medical device controller with the physical location associated with the respective one of the plurality of computer network devices in the second electronic data store;

transmitting, by the one or more servers, via the computer network, to a monitoring station, a physical location of one of the plurality of medical device controllers that was learned by the plurality of machine learning modules; and adjusting, with the one medical device controller, a speed setting or a motor current value of the heart pump communicatively coupled to the one medical device controller, wherein the adjusting of the speed setting or the motor current value is responsive to an alarm being triggered by the operational data extracted from one of the received messages, and wherein the one received message was received from the one medical device controller.

14. The method of claim 13, wherein, for each received message, the respective image comprises a serial number, a placement signal, a speed setting, a motor current value, a blood flow rate, and one or more graphs.

15. The method of claim 14, wherein the respective image of the one received message further comprises an error message.

16. The method of claim 13, wherein the speed setting of the heart pump communicatively coupled to the one medical device controller is adjusted.

17. The method of claim 13, wherein the motor current value of the heart pump communicatively coupled to the one medical device controller is adjusted.

18. The method of claim 13, further comprising:

adjusting a position of the heart pump communicatively coupled to the one medical device controller, wherein the adjusting of the position is responsive to the alarm being triggered.

19. The method of claim 13, further comprising:

restarting the heart pump communicatively coupled to the one medical device controller, wherein the restarting is responsive to the alarm being triggered.

20. The method of claim 13, further comprising:

dispatching medical personnel to the physical location of the one medical device controller that was learned by the plurality of machine learning modules, wherein the dispatching is responsive to the alarm being triggered.

* * * * *